United States Patent
Nagar et al.

(10) Patent No.: US 7,642,060 B2
(45) Date of Patent: Jan. 5, 2010

(54) RAPID RESUSCITATION, GROWTH, CAPTURE AND DETECTION OF MICROORGANISMS

(75) Inventors: Mandar S. Nagar, Stewartstown, PA (US); Edward C. McFarland, Baltimore, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 46 days.

(21) Appl. No.: 11/860,442

(22) Filed: Sep. 24, 2007

(65) Prior Publication Data

US 2008/0182272 A1  Jul. 31, 2008

Related U.S. Application Data

(63) Continuation of application No. 09/841,978, filed on Apr. 25, 2001, now abandoned.

(51) Int. Cl.
 *G01N 33/53* (2006.01)

(52) U.S. Cl. .......................... 435/7.2; 435/4; 435/7.32; 436/518; 436/526; 436/527; 436/528; 436/534; 436/525

(58) Field of Classification Search .................. None
See application file for complete search history.

(56) References Cited

U.S. PATENT DOCUMENTS

| | | | |
|---|---|---|---|
| 3,881,993 A | 5/1975 | Freake et al. | |
| 5,100,801 A | 3/1992 | Ward, Jr. et al. | |
| 5,145,786 A | 9/1992 | Bailey et al. | |
| 5,296,370 A | 3/1994 | Martin et al. | |
| 5,411,867 A | 5/1995 | Chang et al. | |
| 5,443,987 A | 8/1995 | DeCicco et al. | |
| 5,462,860 A | 10/1995 | Mach | |
| 5,510,243 A | 4/1996 | Boyd et al. | |
| 5,648,227 A | 7/1997 | Basbøll | |
| 5,821,066 A | 10/1998 | Pyle et al. | |
| 5,843,699 A | 12/1998 | Strenkoski et al. | |
| 5,976,827 A | 11/1999 | Jeffrey et al. | |
| 6,197,577 B1 | 3/2001 | Jeffrey et al. | |

FOREIGN PATENT DOCUMENTS

| | | |
|---|---|---|
| EP | 0 333 253 | 9/1989 |
| EP | 0 877 092 | 11/1998 |
| WO | WO 95/06256 | 3/1995 |
| WO | WO 94/29696 | 12/1995 |
| WO | WO 96/40981 | 12/1996 |
| WO | WO 00/03035 | 1/2000 |
| WO | WO 00/23792 | 4/2000 |

OTHER PUBLICATIONS

International Biological Products, Tecra Unique™, commercially available *Salmonella* assay system, www.intlbioproducts.com.
Difco Laboratories, *1996/97 Product Catalog for Microbiology*, p. 37.
Poppe et al., "Comparison Of Detection Of *Salmonella* By The Tecra$^R$ Unique™ *Salmonella* Test And The Modified Rappaport Vasslliadis Medium", *Food Microblology*, 1996, 13(1):75-81.
Weimer et al., "Solid-Phase Capture of Proteins, Spores, And Bacteria", *Applied and Environmental Microbiology*, Mar. 2001, 67(3):1300-1307.

*Primary Examiner*—Patricia A Duffy

(57) ABSTRACT

A method and system for the detection and identification of a target pathogen in a sample is disclosed. The method and system involve the use of a capture matrix throughout resuscitation, growth, and detection. The method includes the steps of: placing the sample in a sampling container containing a medium (preferably a growth/resuscitation medium); optionally homogenizing the sample; placing a capture matrix in the sampling container with the sample; incubating the sample in the medium for a pre-determined amount of time at an appropriate temperature; optionally removing the capture matrix from the sampling container; and detecting the presence of the target pathogen in the sample.

18 Claims, No Drawings

RAPID RESUSCITATION, GROWTH, CAPTURE AND DETECTION OF MICROORGANISMS

CROSS REFERENCE TO RELATED APPLICATIONS

This application is a continuation application of U.S. Ser. No. 09/841,978, filed Apr. 25, 2001 now abandoned, the entire contents of which are incorporated by reference herein.

BACKGROUND OF THE INVENTION

1. Field of the Invention

The present invention relates to a method and system for detecting the presence of pathogenic microorganisms in a sample. More specifically, the present invention relates to a method and system for rapidly detecting and identifying target pathogenic microorganisms in a sample that involves the use of a capture matrix throughout the resuscitation, growth and detection processes.

2. Background of the Technology

Each year, millions of persons experience food borne illness caused by pathogenic microorganisms. Only a fraction seeks medical care and even a smaller number submit laboratory specimens. Food borne illness is a continuing threat to all persons, regardless of age, race, sex, lifestyle, ethnic background and socioeconomic status. Food borne illness causes suffering and death and imposes a financial burden on society. The annual national cost associated with food borne illness ranges from 2.9 to 6.7 billion dollars. This range is mainly for the combined direct and indirect costs associated with food borne illness caused by six pathogens: *Campylobacter jejuni* or *Campylobacter coli*; *Clostridium perfringens*; *E. coli* O157:H7; *Listeria monocytogenes*; *Salmonella* (non-typhoid); and *Staphylococcus aureus*.

It has long been recognized that the potential for pathogenic microorganism (pathogen) contamination exists in products which are designed for human consumption or use.

These pathogens are generally present in the colon, intestines or fecal matter of humans or animals. When food products such as poultry, red meat, seafood, eggs or any foods which contain these products, come into contact with fecal matter during handling or processing, the potential exists for contamination and subsequent transfer of the pathogens to the end user.

Not only can the presence of sufficient numbers of pathogens cause the deterioration or spoilage of a food product, such can also cause disease if consumed by a human or animal. While most human cases of bacterial food poisoning only result in acute symptomatic disease, e.g., nausea, vomiting, diarrhea, chills, fever and exhaustion; for individuals such as infants, the elderly, pregnant women, neonates and the immunocompromised, death can occur.

In order to prevent the transmission of food borne pathogens, the manufacturers and/or processors of food products routinely test samples of their products as well as processing equipment to identify contamination before placing a product into the stream of commerce. Typically, pathogens such as enteric bacteria, i.e., Enterobacteriaceae, such as *Salmonella* and *E. coli*, and Gram positive organisms, such as *Staphylococcus* and *Enterococcus*, are the organisms tested for. Because pathogens can be present in very small numbers in a food product which may contain a large number or variety of other non-pathogenic microorganisms, methods for the recovery and detection of pathogens have been developed.

Pathogens are typically injured during processing of products. That is, the pathogens may have undergone heating, freezing, contact with chemical additives, or mechanical processing steps which injure or debilitate the pathogens. Thus, resuscitation of the pathogens before detection is often required.

A primary technique for screening for the presence of pathogens involves the use of a series of media (i.e., nutrient fluid) transfers starting from the use of a non-selective enrichment medium, and then the use of a selective medium. The non-selective enrichment medium is usually employed to resuscitate potentially injured pathogens. Once the pathogens have been revived, a small quantity of the non-selective enrichment medium is then transferred into the selective medium. This technique, which is often defined by human work patterns and the growth patterns of the pathogens, generally takes several days to complete.

For example, culturing a food sample for the presence of *Salmonella* typically involves the addition of approximately 20-25 grams (g) of sample, such as meat, into approximately 225 milliliters (ml) of non-selective enrichment medium, e.g., Buffered Peptone Water (BPW) or Universal Pre-enrichment Broth (UPB), to allow for repair of injured microorganisms. The sample is thoroughly mixed with non-selective enrichment broth and incubated for up to about 22-28 hours at approximately 35 C+/−2 C. Following this step, the sample is further selectively enriched in a growth promoting medium containing inhibitors that allow for the continued growth of a target pathogen, while simultaneously restricting the proliferation of most other competing microorganisms, and further incubated for up to an additional 22-28 hours at approximately 35 C. This secondary enrichment step is generally followed by a detection step that can include plating the secondary enrichment broth onto solid media or by utilizing other methods, such as the use of specific enzyme markers, biochemical testing, immunological assays or DNA probes.

Over the years, many attempts have been made to shorten the length of the primary enrichment step to reduce total assay time. Generally, it has been found that at least 6 to 12 hours of non-selective enrichment is required to obtain enough viable pathogens for further testing.

U.S. Pat. No. 5,145,786 discloses a five step method for the recovery of pathogens. The first step is a pre-enrichment, wherein the food sample is enriched in a non-selective medium to restore injured pathogenic cells to a stable physiological condition. The second step involves a selective enrichment wherein inhibitory reagents are added to the growth medium to promote the growth of the selected pathogens while restricting the proliferation of most other bacteria. The third step involves plating a sample of the enriched growth medium onto a solid selective media to physically isolate pure, discrete colonies of the suspected pathogen. The fourth step involves biochemical testing or screening of the pure cultures obtained from the selective plating step in order to eliminate non-target or competing organisms. The fifth step involves a serological analysis of the pure culture of suspected pathogen in order to specifically identify pathogen(s) present in the sample A major disadvantage of this method, which takes from 3 to 6 days to complete, is that it is very labor intensive and time consuming. This lengthy analysis is often not suitable for producers of perishable products because the producers must keep the products from consumers until the test period is over.

In order to reduce the amount of time for detection, other methods have been developed. The REVEAL® *Salmonella* Test System (Neogen Corp., Lansing, Mich., U.S. Pat. No. 5,296,370) shortens the time frame necessary to approximately two days. On day one, a sample to be tested is inoculated into a non-inhibitory pre-enrichment medium. After approximately two to four hours of incubation, highly selective inhibitors are added to enrich only for specific bacterial pathogens while inhibiting the proliferation of other microorganisms present in the sample. On day two, the samples are assayed by specific immunoassay in order to detect positive and negative samples. All positive samples are then tested further in order to confirm their identity.

U.S. Pat. No. 5,843,699 discloses a method for the detection and identification of target pathogens in a sample which may contain both target pathogens and competing non-target microorganisms. The method involves liquid enrichment of a sample to be tested in order to adjust the levels of the target pathogens in the enrichment medium to be at or above the level of other microorganisms and subsequent biochemical identification.

U.S. Pat. No. 5,296,370 discloses a repair medium that includes a non-selective nutrient medium supplemented with one or more antioxidants, a yeast derivative, an agent capable of reducing oxygen tension in the medium and one or more fatty acids.

U.S. Pat. No. 5,100,801 discloses an apparatus for selective microbial enrichment. The apparatus may include a means for screening liquid between a collection chamber and container. The means for screening acts as a barrier for large particulate materials but not for the target pathogens.

U.S. Pat. No. 5,145,786 discloses a pre-enrichment broth that comprises tryptone, proteose peptone, glucose, sodium pyruvate, ferric ammonium citrate, sodium chloride, magnesium sulfate and buffer salts.

U.S. Pat. No. 5,411,867 discloses a low pH media that contains trimethylamine-N-oxide that promotes the growth of chlorine or food processed injured $E.$ $coli$. The broth may be used in combination with known membrane filtration techniques, which involve capturing bacteria on a membrane filter and transferring the membrane filter to a petri dish containing the media to enable the bacteria to form large colonies.

U.S. Pat. No. 5,443,987 discloses a detection system that can be positioned in-situ in a health care product or can be associated with the health care product packaging such that microbial contamination can be detected.

U.S. Pat. No. 5,462,860 discloses a conditioned culture medium that includes gelatin, casein or animal peptones, yeast extract, carbohydrates, salts and indicators. The conditioned culture medium may be coated onto a self-supporting waterproof substrate, dried and inoculated with sample for detection of pathogen when an added indicator changes color in the presence of selected metabolites.

U.S. Pat. No. 5,510,243 discloses a method for the detection of $E.$ $coli$ in a sample. The method involves capturing the target bacteria on a filter membrane and placing the filter membrane in contact with a semi-solid nutrient medium on a solid support.

Although there are pathogen detection methods in existence, none of them provide a simple and rapid detection of pathogens. Thus, there remains a need for a rapid, sensitive, specific, user friendly, and cost effective method for pathogen detection

SUMMARY OF THE INVENTION

The invention solves the above-identified need by providing a method and system that rapidly detects pathogens in a sample.

The method and system involve the use of a capture matrix throughout the resuscitation, growth and detection processes.

In accordance with one embodiment of the present invention, the method and system include the steps of: placing a sample in a container containing a resuscitation/growth medium; optionally homogenizing the sample; placing a capture matrix in the sampling bag with the sample; incubating the sample in the resuscitation/growth medium for a pre-determined amount of time at an elevated temperature while optionally shaking; optionally removing the capture matrix from the container; performing detection assays to detect the presence of the target pathogens in the sample.

The method and system of the present invention permit detection of as low as 1 colony forming unit (cfu) of target pathogen in 25 g of sample within approximately 4-6 hours. The method and system of the present invention also permit culturing of target pathogens for further identification and stereotyping.

The method and system of the invention thus involve the capture, resuscitation, growth and detection of pathogens on a single capture matrix.

According to another embodiment, the invention involves the use of a capture/test device that can be placed inside a container, e.g., a sampling bag, before or after homogenizing the sample. The capture/test device should be easily retrievable for rapid detection. The capture/test device may be a two-part device containing reagents for a presence/absence test. The presence/absence test may be run on one part of the two-part device and, if present, the other part of the two-part device can be used for culturing and confirming target pathogen(s) using, but not limited to, detection methodologies, such as enzyme-linked immunosorbent assay (ELISA), polymerase chain reaction (PCR), or manual strand displacement amplification (SDA).

Other advantages of the present invention will be readily appreciated as the same becomes better understood by reference to the following detailed description.

DETAILED DESCRIPTION OF THE INVENTION

As discussed herein, pathogens are often subjected to unfavorable growth conditions during transportation and/or processing. Intrinsic factors that affect the growth of pathogens include nutrients, growth factors/inhibitors, water activity, pH, redox potential and oxygen concentration. Extrinsic factors that affect the growth of pathogens include temperature, relative humidity and gases in the surrounding environment. As a result, the pathogens are often sublethally injured due to physical and chemical treatment.

Sublethally injured pathogens are far more sensitive than non-injured pathogens to selective agents in media conventionally used for selective isolation of target pathogens. Due to their increased sensitivity, sublethally injured pathogens can go undetected using conventional detection methodologies. These undetected pathogens carry a potential to multiply at a later stage, causing illness. The undetected pathogens can also deny proper treatment to a patient via false negative laboratory reports.

For the reasons discussed above, it is critical to resuscitate sublethally injured target pathogens before growth. The method and system of the invention involve the use of a capture matrix throughout the resuscitation, growth and detection processes. According to one embodiment, a conventional resuscitation/growth medium, e.g., modified Tryptic Soy Broth (TSB), is used in combination with a capture matrix inside a container, e.g., a sampling bag, and the capture, resuscitation and growth of the injured target pathogen occurs on the capture matrix. The method and system of the invention facilitate the repair of sublethal injuries to target pathogens. Once the injury is repaired, the resuscitation/growth medium provides nutrition for vigorous growth of the resuscitated pathogen.

The method and system of the invention can be carried out in a number of settings, including clinics (e.g., for Mycobacteria); environmental labs (e.g., for coliforms, *Cryptosporidium*); and for bio-defense (e.g., *Brucella anthrax*). The method and system of the invention can also be used during transportation of a test sample (e.g., soil, etc.) from the collection site to the testing laboratory. This may be achieved by placing the capture matrix inside a sampling/transportation device containing suitable resuscitation/growth medium, thus facilitating the capture, resuscitation and growth of the target pathogen for rapid detection.

In addition, the method and system of the invention can act as a delivery system for delivering captured pathogens of interest to a multitude of detection methodologies.

The method of the invention provides many advantages over currently employed methods, including:

(1) The method and system of the invention involves the use of conventional materials that are normally used in a laboratory.

(2) The capture matrix within the sampling container increases the probability of capturing and concentrating a very low number of target pathogens compared to other methodologies.

(3) The capture matrix within the sampling container reduces sampling issues when very low numbers of target pathogens are present at the time of sampling.

(4) The captured, resuscitated and grown target pathogens can be detected within 4-6 hours, which is approximately 2-4 hours faster than prior known methods.

(5) With a multi-pathogen capture device, multiple target pathogens can be captured and detected using a single test.

(6) The captured target pathogens can be cultured for further identification/confirmation/stereotyping.

(7) Capturing target pathogen(s) on a matrix negates the need to further process the test sample (e.g., by filtration, digestion, etc.).

The method and system of the present invention thus permit rapid screening for detection and identification of target pathogen(s) in a sample that contains both target pathogen(s) and competing non-target microorganisms. In particular, the method of the present invention includes placing a sample in a container containing a medium, incubating the sample in the presence of a capture matrix, and performing detection assays on the capture matrix to detect the target pathogen. It is also possible to use the capture matrix to concentrate the specific pathogen.

Target pathogens that can be detected and identified using the method and system of the present invention include Gram (−) organisms such as the Enterobacteriaceae, including *E. coli*, and Gram (+) organisms, including *Staphylococcus aureus* and *Enterococcus faecalis*.

For example, in testing a food sample, the rapidly growing target pathogens that could be tested for could include, but are not limited to, *Salmonella* and/or *E. coli*. Since these pathogens which are often found in a variety of foods (e.g., ground beef, milk, cheese, vegetables, apple cider, etc.), they are often "targeted" for testing in order to determine if they are present in a food sample.

The container holding the test sample may be one container, with either a single cavity or multiple cavities, a container with a screen mesh in the center, or two separate containers attached to each other through a channel that can be broken to release materials within. Additionally, the container may have a sachet attached to it that contains reagents. The capture matrix could be added to the container, could be "built in", or could be present in the channel connecting or separating two separate containers.

In a preferred embodiment, the container is constructed in the form of a single bag with a screen mesh to separate particulate materials from the test liquid. The capture matrix is a detection strip that is added to the container (preferably after homogenation), and then removed for detection. The bag can be constructed of any suitable resilient plastic material such as a polyester/polyethylene laminate, but it can also be made of any other suitable material known to those skilled in the art. Because of the nature of the samples which may be tested, such as a food sample, the container should be constructed of a resilient material so that it can withstand homogenizing or "stomaching" of the sample disposed within the bag in order to expose the microorganisms within the sample.

The medium located inside the container is not particularly limited, and includes items such as a growth medium, a buffer, water, solvent, semi-solid growth medium, resuscitation medium, a process solution, or a simple growth medium A resuscitation/growth medium is most preferred.

The resuscitation/growth medium can include any general, non-selective and/or mildly selective growth medium known to those skilled in the art, including REVIVE® (Neogen Corp., Lansing, Mich.) Tryptic Soy Broth, TSB (Difco), or other similar type medium. The preferred resuscitation/growth medium for use in the present invention is TSB.

The resuscitation/growth medium can also include a selective inhibitor or mildly selective inhibitor or mixtures thereof. Inhibitors are selective agents used for the simultaneous restriction of "non-target" organisms. Single selective agents or combinations of inhibitors can be used. For example, the antibiotic novobiocin can be added to the container prior to the addition and incubation of the sample in order to provide a selection pressure in favor of the growth of *Salmonella*. Suitable examples of inhibitors include, but are not limited to, antibiotics that selectively inhibit gram positive organisms (e.g., novobiocin, tylosin, etc.), chemicals that selectively inhibit gram positive organisms (e.g., bile salts, sodium pyridine, sodium selenite, ferric citrate, sodium citrate, sodium deoxycholate, sodium taurocholate, magnesium chloride, tergitol-4 (XLT4), etc.), chemicals that selectively inhibit gram negative microorganisms (e.g., lithium chloride, solistin sulfate, cefotetan fosfomycin, sodium azide, etc.), dyes (e.g., malachite green crystal violet, brilliant green, etc.), chloramphenicol, chlortetracycline, cycloserine, cefoxitoxin, kanamycine, oxytetracycline, polymyxin-B, anti-fungal agents, and anti-parasite agents. Other target pathogen selection enhancing additives known to those skilled in the art can be added to the resuscitation/growth medium to favor the growth of the selected target pathogen(s) over other competing non-target microorganisms present in the sample.

The selective inhibitor(s) or mixtures thereof can include compounds or reagents which are known to inhibit the growth of non-target microorganisms while encouraging the proliferation or growth of the target pathogen(s). For example, if the target pathogen is *Salmonella*, it is known that a mixture of magnesium chloride, malachite green, and crystal violet can be added to the pre-enrichment media to yield excellent inhibition of non-target microorganisms. The concentration of the malachite green in the solution ranges from approximately 10 mg/l to 50 mg/l (0.003%-0.03 w/v), the magnesium chloride concentration ranges from approximately 0.5 g/l to approximately 2 g/l (0.1%-1.0% w/v), and the concentration of the crystal violet ranges from approximately 0.001 g/l to 0.010 g/l (0.0005%-0.001% w/v). The preferred concentration of the inhibitor mixture for *Salmonella* includes 30 mg/l malachite green, 0.005 g/l crystal violet, and approximately 1.0 g/l magnesium chloride. Other inhibitors include bile salts, sodium deoxycholate, sodium selenite, sodium thiosulphate, sodium tetrathionate, sodium sulphacetamide, mandelic acid, tetrathionate, sulphamethazine, brilliant green, malachite green, crystal violet, tergitol 4, sulfadiazine, amikacin, and novobiocin.

The capture matrix used to capture target pathogens may be added to the container prior to or subsequent to the addition of the test sample. Alternatively, the capture matrix may be an intricate part of the container itself. The capture matrix is not limited to any particular material or substance, so long as the capture matrix binds and/or absorbs proteinaceous materials. For example, the capture matrix could be nitrocellulose membranes spotted with capture antibodies, cellulose gauze, hydroxyapatite, or magnetic beads coated with capture antibodies that are attached to a magnetic strip and separated by a non-magnetic layer so that the beads can be released into a tube after capture by removal of the magnetic strip. Suitable examples of the capture matrix include plastic surfaces, latex microparticles, porous membranes, paper, woven materials, glass, metals, magnetic beads, dextran, dextran particles, and agarose.

Following the dispensing of the sample in the container, the sample can be stomached or homogenized within the bag utilizing means well known to those skilled in the art, (e.g., via Stomacher Lab-Blender, Seward Medical, London, U.K.). The sample is stomached/homogenized within the bag containing the resuscitation/growth medium. The container is incubated in the presence of the capture matrix at a temperature suitable for growth of the target pathogen. The incubation of the sample is carried out to resuscitate and grow sublethally injured pathogens present in the sample.

At the end of the incubation period, specific detection assays can be performed on the capture matrix to detect the presence of the target microorganism.

One method of detection is through the use of biochemical tests or assays. Examples of biochemical assays include enzyme detection, products of bacterial metabolism, immunochemical markers, specific stains, chemiluminescence, and bioluminescence. Biochemical tests or reagents specific for identification and/or detection of the target pathogen can include antibiotics, dyes, and other biochemical reagents indicative of particular pathogen such as by targeting sugar fermentation, decarboxylation, cleavage by unique enzymes, and/or use of unique combinations of dyes (including fluorescent dyes). Additionally, other reagents used in the detection and identification of pathogens known to those skilled in the art may be practiced with the present invention. For example, for the detection of *Salmonella*, the capture matrix can be transferred into a container containing reagents necessary for performing a MUCAP (methylumbelliferyl caprylate) test. Additional containers may be utilized which contain reagents for further biochemical tests such as $H_2S$ tests, media specifically designed to indicate the presence of lysine decarboxylase, ornithine decarboxylase, or arginine decarboxylase in a suitable base media such as LICNR (lysine-iron-cystine-neutral red broth, Difco Manual) base media, fermentation reaction media such as for dulcitol, propylene glycol (PG), glucuronic acid (GA), in a peptone base, and a citrate utilization can also be assayed using Simmon's citrate agar (Difco Manual) or citrate medium (magnesium sulfate, ammonium dihydrogen phosphate, sodium citrate, yeast extract, sodium chloride) placed in the media receiving vessels.

Alternatively, the pathogens may be detected by a change in pH, an immunological reaction, detection of fluorescence, chemiluminescence, growth on agar or other solid surface, calorimetric quantitation, or other detection technique known by one of ordinary skill in the art. Detection can occur inside the container or outside the container, and may or may not need additional reagents or treatment for completion.

The present invention also includes a kit containing the sampling container, resuscitation/growth medium, the capture matrix, optionally selective inhibitors, and specific biochemical assay reagents necessary for performing the detection of target pathogen(s), all of which have been described above.

The invention will now be illustrated by the following non-limiting example.

EXAMPLE

A feasibility study showed the capture of target pathogen from an artificially inoculated food sample. A 25 g aliquot of ground beef with 22% fat was artificially inoculated with different levels of *E. coli* O157:H7 pathogen. The target pathogen was captured directly from a stomacher bag via immobilized capture antibodies on a capture matrix placed inside the stomacher bag. The following protocol was used:

(1) 25 g ground beef with 22% fat was placed in each of five sterile Whirl-Pak stomacher bags;

(2) 225 ml resuscitation/growth medium was added to each bag;

(3) one sample of each of 5 levels of *E. coli* O157:H7 was added to each of the bags;

(4) the bags were stomached/homogenized for 30 seconds;

(5) a capture matrix (i.e., immobilon-P membrane spotted with goat anti-*E. coli* O157:H7 antibodies) was placed inside each of the bags;

(6) the bags were incubated at 37 C for 5 hours with shaking at ~100 rpm;

(7) the capture matrix was retrieved from each bag; and (8) target pathogens captured on the capture matrix were detected.

The sensitivity of the capture protocol from ground beef was found to be around 50 cfu total per bag (desired: 1 cfu/225 ml) at the beginning of the test (T0). The total bioburden of the ground beef sample was observed to be at about $2 \times 10^3$ cfu/ml at T0. The immunocapture was detected by placing each washed capture matrix upside down onto the surface of BBL CHROMagar 0157 with an overnight incubation at 37° C. Presence of circular mauve growth under spotted capture antibodies indicates a positive capture.

As discussed herein, the method and system of the invention can also be used as a delivery platform for delivering organisms of interest to various detection methodologies. Not only food pathogens, but clinical, industrial, and environmental pathogens, as well as pathogens involved in bio-terrorism, can be captured and detected rapidly in accordance with the method and system of the invention. A few detection methodologies described below can be used in association with the method and system of the invention:

(a) The stomached/homogenized test sample containing target pathogen may be forced through a narrow capture-cartridge type device holding immobilized capture antibodies. The increased interaction between target pathogen and capture matrix facilitates capture.

(b) A capture device coated with capture matrix (e.g., a fluorescently labeled antibody) can be inserted into the solid/liquid test sample or inside the pre-enriched test sample in stomacher bag/sampling device to capture/detect target pathogen.

(c) Flow cytometry can be used to automate the method and system of the invention. Improved discrimination against non-specific fluorescence due to particulate matter may be achieved by using improved fluorophores and viability markers. The measurement of DNA content may also allow for better discrimination of the pathogens of interest.

It is apparent that the method and system of the present invention can be applied to growing cells other than bacteria. For example, eukaryotic cells grown in tissue culture and which either produce an excreted protein, such as an antibody (e.g., plasma cells and B lymphocytes), or which are marked by specific cell surface constituents, can be subjects of the present invention. It should also be clear that many capture and detection methods are within the scope of the invention.

Having now fully described the invention with reference to certain representative embodiments and details, it will be apparent to one of ordinary skill in the art that changes and modifications can be made thereto without departing from the spirit or scope of the invention as set forth herein.

The invention claimed is:

1. A method for detecting the presence or absence of a target pathogen in a sample, comprising:
    placing the sample in a sampling container with a resuscitation and/or growth medium, without performing a separate non-selective enrichment step, wherein the resuscitation and/or growth medium inside the sampling container comprises a selective growth medium;
    incubating the sample in the resuscitation and/or growth medium in the container, in the presence of a capture matrix, said capture matrix containing an antibody for the target pathogen, wherein the sample is incubated for a length of time and at a temperature suitable for resuscitation and/or growth of the target pathogen, and the capture matrix is present throughout the resuscitation and/or growth process; and
    removing said capture matrix from the resuscitation and/or growth medium in the container and performing a detection assay on said capture matrix removed from the resuscitation and/or growth medium to detect the target pathogen.

2. The method of claim 1, wherein said sample is homogenized prior to incubation.

3. The method of claim 1, wherein detection occurs by a biochemical assay, a change in pH, an immunological reaction, fluorescence detection, chemiluminescence or colorimetric quantitation.

4. The method of claim 3, wherein said detection assay is a biochemical assay specific for detection of the target pathogen.

5. The method of claim 4, wherein said biochemical assay is selected from the group consisting of enzyme detection, products of bacterial metabolism, immunochemical markers, specific stains, chemiluminescence and bioluminescence.

6. The method of claim 1, wherein said capture matrix is placed in the sampling container subsequent to the placement of the sample in the sampling container.

7. The method of claim 1, wherein said capture matrix is part of the sampling container.

8. The method of claim 1, wherein said incubation lasts between 1 minute and 120 minutes.

9. The method of claim 1, wherein said incubation lasts between 1 hour and 72 hours.

10. The method of claim 1, wherein said incubation lasts up to 6 weeks.

11. The method of claim 1, wherein said sampling container is a bag with a screen mesh, said capture matrix includes a detection strip, and said detection strip is removed prior to detection of the target pathogen.

12. The method of claim 1, wherein said sampling container is selected from the group consisting of a container having a single cavity, a container having multiple cavities, a container with a screen mesh and two separate containers attached to each other by a channel to form a single unit.

13. The method of claim 1, wherein said container is a bag.

14. The method of claim 1, wherein said capture matrix is selected from the group consisting of plastic surfaces, latex microparticles, porous membranes, paper, woven materials, glass, metals, magnetic beads, dextrans, dextran particles and agarose.

15. The method of claim 14, wherein said capture matrix is selected from the group consisting of nylon, nitrocellulose and polysulphone.

16. The method of claim 1, wherein said resuscitation and/or growth medium includes an inhibitor.

17. The method of claim 16, wherein said inhibitor is selected from the group consisting of novobiocin, tylosin, bile salts, sodium pyridine, sodium selenite, ferric citrate, sodium citrate, sodium deoxycholate, sodium taurocholate, magnesium chloride, tergitol-4, lithium chloride, colistin sulfate, cefotetan, fosfomycin, sodium azide, malachite green, crystal violet, brilliant green chloramphenicol, chlortetracycline, cycloserine, cefoxitin, kanamycine, oxytetracycline and polymyxin-B.

18. The method of claim 1, wherein said sampling container is a transportation device.

* * * * *